(12) United States Patent
Cizmar et al.

(10) Patent No.: US 12,629,004 B2
(45) Date of Patent: May 19, 2026

(54) MULTIMODE OPTICAL FIBER, ENDOSCOPIC SYSTEM AND METHOD FOR EXAMINING A SAMPLE

(71) Applicant: LEIBNIZ-INSTITUT FUR PHOTONISCHE TECHNOLOGIEN E.V., Jena (DE)

(72) Inventors: Tomas Cizmar, Weimar (DE); Beatriz Silveira, Jena (DE)

(73) Assignee: LEIBNIZ-INSTITUT FUR PHOTONISCHE TECHNOLOGIEN E.V., Jena (DE)

( * ) Notice: Subject to any disclaimer, the term of this patent is extended or adjusted under 35 U.S.C. 154(b) by 277 days.

(21) Appl. No.: 18/275,083

(22) PCT Filed: Jan. 28, 2022

(86) PCT No.: PCT/EP2022/052041
§ 371 (c)(1),
(2) Date: Jul. 31, 2023

(87) PCT Pub. No.: WO2022/162140
PCT Pub. Date: Aug. 4, 2022

(65) Prior Publication Data
US 2024/0090750 A1      Mar. 21, 2024

(30) Foreign Application Priority Data
Jan. 29, 2021    (DE) .................... 10 2021 102 091.3

(51) Int. Cl.
*A61B 1/00*          (2006.01)
*A61B 1/05*          (2006.01)
(Continued)

(52) U.S. Cl.
CPC ........ *A61B 1/0017* (2013.01); *A61B 1/00167* (2013.01); *A61B 1/05* (2013.01); *A61B 1/0676* (2013.01); *A61B 1/07* (2013.01)

(58) Field of Classification Search
CPC ........... A61B 1/00165; A61B 1/00167; A61B 1/0017; A61B 1/07; G02B 6/262; G02B 6/3624
See application file for complete search history.

(56) References Cited

U.S. PATENT DOCUMENTS 3,675,984 A * 7/1972 Vulmiere ........... A61B 1/00165
385/902
5,030,207 A * 7/1991 Mersch ............ A61B 5/150389
604/168.01

(Continued)

FOREIGN PATENT DOCUMENTS

DE          198 04732 A1      8/1988
DE          695 25 392 T2    10/2002
(Continued)

OTHER PUBLICATIONS

International Search Report and Written Opinion mailed on Jun. 9, 2022 for International Patent Application No. PCT/EP2022/052041 w/English Translation.

(Continued)

*Primary Examiner* — Michael J Carey
*Assistant Examiner* — Stephen Floyd London
(74) *Attorney, Agent, or Firm* — HUNTON ANDREWS KURTH LLP

(57) ABSTRACT

The invention relates to a multimode optical fiber (1) with an optical axis (2). The multimode optical fiber has a single fiber core (11) surrounded by a cladding (12) and comprises a proximal end (3) for connection to an endoscopic system (13) and a distal end (4) for introduction into a sample (14). The distal end (4) has a light transmission surface (5), which (Continued)

extends substantially parallel to the optical axis (2) and is designed to transmit light radially in relation to the optical axis (2). The light transmission surface (5) is a substantially flat surface, a spherical segment surface or a paraboloid segment surface, and is a boundary surface of the fiber core (11). In addition, the distal end (4) has a light reflection surface (6), which extends such that the optical axis (2) at the distal end (4), a normal to the light transmission surface (5) and a normal to the light reflection surface (6) lie substantially in one plane and an angle between the light reflection surface (6) and the optical axis (2) is between 30° and 60°. In addition, the invention relates to an endoscopic system (13) for examining a sample (14) and to a method for examining a sample (14) by means of an endoscopic system (13).

6 Claims, 7 Drawing Sheets

(51) Int. Cl.
     *A61B 1/06*          (2006.01)
     *A61B 1/07*          (2006.01)

(56)                    References Cited

U.S. PATENT DOCUMENTS

| | | | | |
|---|---|---|---|---|
| 5,772,657 | A | 6/1998 | Hmelar et al. | |
| 5,831,743 | A * | 11/1998 | Ramos | G01F 1/661 |
| | | | | 385/85 |
| 5,964,747 | A | 10/1999 | Eaton et al. | |
| 6,174,424 | B1 * | 1/2001 | Wach | G01N 21/7703 |
| | | | | 205/79 |
| 10,743,749 | B2 | 8/2020 | Yamada | |

| | | | | |
|---|---|---|---|---|
| 2006/0198418 | A1 * | 9/2006 | Hama | G02B 6/262 |
| | | | | 372/6 |
| 2007/0116408 | A1 * | 5/2007 | Eberle | A61B 5/0095 |
| | | | | 385/38 |
| 2012/0099112 | A1 * | 4/2012 | Alphonse | G01B 9/02044 |
| | | | | 385/12 |
| 2012/0283523 | A1 * | 11/2012 | Yadlowsky | G02B 6/262 |
| | | | | 600/249 |
| 2016/0278694 | A1 * | 9/2016 | Aharoni | A61B 5/6848 |
| 2018/0307035 | A1 * | 10/2018 | Kobayashi | G02B 23/2469 |
| 2021/0262632 | A1 * | 8/2021 | Chen | F21S 41/285 |
| 2022/0061644 | A1 * | 3/2022 | Fontaine | A61B 5/745 |
| 2022/0226665 | A1 * | 7/2022 | Uto | A61B 1/07 |

FOREIGN PATENT DOCUMENTS

| | | | | | |
|---|---|---|---|---|---|
| EP | 0163266 | A2 * | 12/1985 | | A61B 1/07 |
| EP | 0689797 | A1 | 1/1996 | | |
| EP | 1513162 | A1 | 3/2005 | | |
| FR | 2 948 007 | A1 | 1/2011 | | |
| FR | 2 948 997 | A1 | 2/2011 | | |
| JP | S61114215 | A | 5/1986 | | |
| JP | 2004258387 | A | 9/2004 | | |
| JP | 2005533610 | A | 11/2005 | | |
| JP | 2009531151 | A | 9/2009 | | |
| JP | 2013506866 | A | 2/2013 | | |
| JP | 2014522483 | A | 9/2014 | | |
| WO | 2007112196 | A2 | 10/2007 | | |

OTHER PUBLICATIONS

European Office Action dated Aug. 21, 2025 for EP Patent Application No. 27 713 288.3, 16 pages.
Japanese Office Action dated Jul. 9, 2024 for JP Patent Application No. 2023-546063, 10 pages.
German Office Action dated Mar. 17, 2021 for DE Patent Application No. 10 2021102 091.3, 7 pages.

* cited by examiner

MULTIMODE OPTICAL FIBER, ENDOSCOPIC SYSTEM AND METHOD FOR EXAMINING A SAMPLE

CROSS REFERENCE TO RELATED APPLICATION(S)

This application relates to, and claims the benefit and priority from International Patent Application No. PCT/EP2022/052041 filed Jan. 28, 2022 that published as International Patent Publication No. WO 2022/162140 on Aug. 4, 2022, which claims the benefit and priority from German Patent Application No. 10 2021 102 091.3 filed on January 29. 2021, the entire disclosures of which are incorporated herein by reference.

FIELD OF THE INVENTION

The invention relates to a multimode optical fiber, to an endoscopic system for examining a sample, and to a method for examining a sample by means of an endoscopic system.

BACKGROUND

Endoscopy with an endoscopic system comprising a multimode optical fiber as probe, what is referred to as holographic endoscopy, offers the possibility of obtaining high-resolution images of samples and in the process only minimally adversely affecting the samples. The samples under consideration here, for example, are animals or humans, it being the case for example that neurons and the neuronal network, inter alia in the brain of these samples, are examined.

In this respect, the minor adverse effect on the samples results from the fact that the multimode optical fibers have a typical diameter of only about 100 µm. However, the sample is slightly damaged along an introduction path of the multimode optical fibers; in the example of animals or humans, the result is an elongate tear in the tissue, and also the tissue directly in front of the multimode optical fiber is damaged by the pressure during the introduction.

In order to obtain good images of the sample in spite of these problems, for example, an image plane located a short distance in front of the multimode optical fiber is examined instead of the damaged regions directly in front of the multimode optical fiber. In the process, the sample is damaged only very slightly if at all in the region of the image plane to be examined. In this respect, however, the problem arises that the examination light must propagate through part of the sample and thus deterioration in the quality of the images is accepted.

SUMMARY

It is an object of the invention to propose a multimode optical fiber, an endoscopic system comprising a multimode optical fiber, and a method for examining a sample by means of an endoscopic system which overcome the aforementioned disadvantages. The object is achieved by the subject matter of the independent patent claims. Refinements of the invention will emerge from the dependent claims and the following description.

One aspect of the invention relates to a multimode optical fiber with an optical axis, comprising a proximal end for connection to an endoscopic system and a distal end for introduction into a sample. In this case, the distal end has a light transmission surface, which extends substantially parallel to the optical axis and is designed to transmit light radially in relation to the optical axis. In addition, the distal end has a light reflection surface, which preferably extends such that the optical axis at the distal end, a normal to the light transmission surface and a normal to the light reflection surface lie substantially in one plane and an angle between the light reflection surface and the optical axis is between 30° and 60°. This aspect of the invention can be combined with all of the embodiments disclosed below.

A further aspect of the invention also relates to a multimode optical fiber. In this respect, a multimode optical fiber is understood to mean an optical fiber or an optical waveguide which has a fiber core of which the diameter is large enough for multiple light modes to be able to propagate therein. Of course, this depends on the wavelength of the light to be used, with use usually being made of light in the range of the visible spectrum, that is to say with wavelengths in the range of approximately 380 nm to 750 nm. As a synonym for the term "multimode optical fiber", it is thus also possible to use the term "optical fiber" or "optical waveguide" within the context of the present invention provided that the fiber core has a sufficiently large diameter.

The multimode optical fiber has an optical axis. If a straight, non-curved multimode optical fiber is assumed, the optical axis corresponds to the axis of rotational symmetry of the multimode optical fiber. The optical axis thus extends in a longitudinal direction of the multimode optical fiber, with the result that the multimode optical fiber appears circular in a cross section perpendicular to the optical axis.

The multimode optical fiber also has a single fiber core surrounded by a cladding. In this case, the fiber core denotes the innermost region of the multimode optical fiber, which includes the optical axis. As a result of the cladding, which cylindrically encloses the fiber core, the total reflection of the light in the fiber core is independent of the medium surrounding the multimode optical fiber and thus, for example, disruptions caused by a changing medium along the multimode optical fiber are prevented. However, it is also conceivable for the cladding to be formed by a graded profile of the refractive index.

In addition, the multimode optical fiber has a proximal end. In this respect, the multimode optical fiber is connected to an endoscopic system by means of the proximal end.

The multimode optical fiber also has a distal end, which is opposite the proximal end. In this respect, the distal end of the multimode optical fiber is introduced into a sample. The sample may be an inorganic or an organic sample, for example an animal or a human.

The distal end of the multimode optical fiber has a light transmission surface which extends substantially parallel to the optical axis. In this case, the direction of the optical axis is understood to mean in the region of the distal end of the multimode optical fiber. Substantially parallel means that an angle between the optical axis and the light transmission surface is less than 15°, in particular less than 10°, very particularly less than 5°. In this respect, the light transmission surface is designed to transmit light radially to the optical axis. It is thus possible both for light to exit the multimode optical fiber through the light transmission surface and for light from outside the multimode optical fiber to enter the multimode optical fiber through the light transmission surface.

In this respect, the light transmission surface is a substantially flat surface. This results in a particularly simple geometry of the multimode optical fiber and thus a simple description of the light profile from the multimode optical fiber via the light reflection surface through the light transmission surface, and back again.

As an alternative to this, the light transmission surface is a spherical segment surface or a paraboloid segment surface. These particular surface shapes result in the focusing of the light being modified and thus may be helpful for special examinations of the sample. In the case of a spherical segment surface or a paraboloid segment surface, the alignments, for example the angles, of the light transmission surface are to be understood in the sense of a plane approximating the light transmission surface.

The light transmission surface is also a boundary surface of the fiber core. That is to say, the fiber core is delimited, among other things, by the light transmission surface.

In addition, the distal end has a light reflection surface. In this respect, the light reflection surface preferably extends such that the optical axis at the distal end, a normal to the light transmission surface and a normal to the light reflection surface lie substantially in one plane. In addition, an angle between the light reflection surface and the optical axis is between 30° and 60°. Light entering the multimode optical fiber through the light transmission surface is thus reflected by the light reflection surface, with the result that it can propagate in the multimode optical fiber along the optical axis. Similarly, light exiting the proximal end of the multimode optical fiber is reflected by the light reflection surface, with the result that it can also exit the multimode optical fiber through the light transmission surface.

Overall, light propagating in the multimode optical fiber along the optical axis is thus deflected in a direction which is radial in relation to the optical axis by the light reflection surface and the light transmission surface. An endoscopic system connected to the multimode optical fiber thus makes it possible to examine regions of the sample which are radial in relation to the optical axis at the distal end of the multimode optical fiber. The introduction of the multimode optical fiber into the sample in particular damages the sample in the region in front of the multimode optical fiber, since the sample material is compressed there. By contrast, there is considerably less damage to the sample material radially in relation to the optical axis, and therefore the examination of the sample in a region which is radial in relation to the optical axis involves undamaged or only slightly damaged sample material. It is therefore not necessary to heal the sample after the multimode optical fiber has been introduced, or such healing can be limited to a short period of time. In addition, the image plane to be examined does not need to be a long way away from the multimode optical fiber, since it is possible to examine the undamaged or only slightly damaged sample material directly in front of the light transmission surface, radially in relation to the optical axis.

In some embodiments, the light transmission surface extends parallel to the optical axis. In that case, an examination of the sample exactly radially in relation to the optical axis is preferred.

In some embodiments, the light transmission surface is inclined by an angle between 2° and 10°, in particular 4° to 6°, in relation to the optical axis. In the case of input and output coupling of light into and out of the multimode optical fiber via the light reflection surface through the light transmission surface, a beam profile of the light which firstly is refracted at the light transmission surface, then is reflected by the light reflection surface, and then is reflected once more by way of total reflection at the light transmission surface is possible in this respect. This makes it possible to input couple light into the multimode optical fiber from a relatively large angular range, thereby enabling a higher optical resolution.

In some embodiments, the angle between the light reflection surface and the optical axis is between 40° and 50°, in particular approximately 45°. In particular in the case of a light transmission surface which extends parallel to the optical axis, a light reflection surface which is inclined by 45° in relation to the optical axis results in optimum input and output coupling of light into and out of the multimode optical fiber. If, by contrast, the light transmission surface is inclined by an angle $\alpha$ in relation to the optical axis, input and output coupling of light perpendicularly to the optical axis is provided when the light reflection surface is inclined by 45° minus half an angle $\beta$ in relation to the optical axis, wherein it holds true that $n_2 \sin (\beta) = n_1 \sin (a)$, where $n_2$ is the refractive index of the multimode optical fiber and $n_1$ is the refractive index of the medium surrounding the multimode optical fiber.

In some embodiments, a sharp edge is formed between the light transmission surface and the light reflection surface. This sharp edge is produced by the convergence of the light transmission surface and the light reflection surface. In this respect, the angle between the light transmission surface and the light reflection surface is between 30° and 60°, in particular approximately 45°. If there is no rounding where the light transmission surface and the light reflection surface converge, this edge is sharp enough to cut through various sample materials and does not merely push the material away when the multimode optical fiber is being introduced into the sample. This further reduces the destruction of the sample material, thereby improving the examination of the sample.

In some embodiments, the light reflection surface is a substantially flat surface. This results in a particularly simple geometry of the multimode optical fiber and thus a simple description of the light profile from the multimode optical fiber via the light reflection surface through the light transmission surface, and back again.

In some embodiments, the light reflection surface is a spherical segment surface or a paraboloid segment surface. These particular surface shapes result in focusing when the light is being input and output coupled into and out of the multimode optical fiber and thus may be helpful for special examinations of the sample. In the case of a spherical segment surface or a paraboloid segment surface, the alignments, for example the angles, of the light reflection surface are to be understood in the sense of a plane approximating the light reflection surface.

In some embodiments, the light transmission surface and/or the light reflection surface are produced by polishing the distal end of the multimode optical fiber. As a result, in particular flat surfaces and spherical segment surfaces can be produced as light transmission surface and/or light reflection surface. In this respect, the smoothness of the surfaces depends on the fineness of the polishing means.

In some embodiments, the light transmission surface and/or the light reflection surface are/is produced by milling, in particular by means of a focused ion beam. Light transmission surfaces and/or light reflection surfaces produced in this way may also have complicated geometries.

In some embodiments, the light reflection surface is provided with a coating, in particular with a dielectric and/or metallic coating. As a result, the reflection coefficient is increased in comparison with an uncoated light reflection surface, with the result that the light yield and thus the quality of images obtained are improved. In this case, the coating is applied to the light reflection surface for example by vapor deposition or by sputtering.

In some embodiments, the light transmission surface is provided with a coating, in particular with a dielectric coating. As a result, it is possible for example to increase the transmission coefficient in comparison with an uncoated light reflection surface, with the result that the light yield is improved, disruptive reflections are reduced and thus overall the quality of images obtained is improved. In this case, the coating is applied to the light reflection surface for example by vapor deposition or by sputtering.

In some embodiments, a diameter of the multimode optical fiber, measured in a cross section perpendicular to the optical axis, is between 50 µm and 300 µm, in particular between 80 µm and 150 µm. In order to keep the diameter of the multimode optical fiber low, which means there is only very little damage to the sample, a thickness of the cladding of the multimode optical fiber is kept low, in particular thinner than 20 µm, very particularly thinner than 10 µm or thinner than 5 µm. While multimode optical fibers with a smaller diameter cause less damage to the sample, a greater number of light modes can propagate in multimode optical fibers with larger diameters, thereby leading to images with a higher resolution.

A further aspect of the invention relates to an endoscopic system for examining a sample. In this respect, the sample may be an inorganic or an organic sample, for example an animal or a human.

The endoscopic system here comprises a coherent light source, a photodetector and a multimode optical fiber, the multimode optical fiber being designed according to the description above.

The coherent light source is for example a laser. The coherent light source is arranged in such a way that it introduces light into the proximal end of the multimode optical fiber. In the process, the light from the coherent light source is preferably modified such that the light modes in the multimode optical fiber are excited in such a way that a single point in a region in front of the light transmission surface at the distal end of the multimode optical fiber is illuminated.

The photodetector is arranged in such a way that it detects light exiting the proximal end of the multimode optical fiber. In this respect, this light is emitted by the point illuminated by the coherent light in the region in front of the light transmission surface and is conducted to the proximal end via the light transmission surface, the light reflection surface and the multimode optical fiber. In order to be able to carry out the illumination and detection at the same time, the coherent light source and the photodetector are incorporated in an optical arrangement of the endoscopic system, for example via a beam splitter.

The advantages of the multimode optical fiber, in particular examination of the sample radially in relation to the optical axis, where the sample material has not been damaged or has been damaged only slightly by the introduction of the multimode optical fiber, are also transferred to the endoscopic system.

A further aspect of the invention relates to a method for examining a sample by means of an endoscopic system according to the description above. In this respect, the sample may be an inorganic or an organic sample, for example an animal or a human. As a result of the high resolution that can be achieved with the endoscopic system, it is suitable for example for the examination of neurons and the neuronal network, for example in the brain of the animal or human.

In the course of the method, the coherent light source is used to illuminate a multiplicity of object points in the sample one after another by way of the multimode optical fiber. The illumination of different object points is effected here by a different modification of the coherent light. Here, the illuminated object points are radial in relation to the optical axis at the distal end of the multimode optical fiber, in front of the light transmission surface. The object points may for example be illuminated one after another in a grid pattern. An answering light that is emitted by the object points and is brought about for example by reflection, fluorescence, Raman scattering, stimulated Raman scattering, coherent anti-Stokes Raman scattering, autofluorescence and/or frequency doubling, re-enters the multimode optical fiber through the light transmission surface, is reflected at the light reflection surface and conducted through the multimode optical fiber to the proximal end. There, the light exits the multimode optical fiber and is detected by means of the photodetector. As a result, the image information for the individual object points is received one item of information after another. It is also possible to illuminate object points in various planes in front of the light transmission surface and thus examine multiple planes of the sample by further modifications of the coherent light.

Since the examined object points are radial in relation to the optical axis at the distal end of the multimode optical fiber, sample material which was not damaged or was only slightly damaged by the introduction of the multimode optical fiber into the sample is examined.

In some embodiments, light transmission properties of the multimode optical fiber are measured before the sample is examined. In the process, preferably the form, for example straight or curved, of the multimode optical fiber in which it then also comes to bear against the sample is maintained. In this respect, defined coherent light is introduced into the multimode optical fiber on one side of the multimode optical fiber and the result is measured on the other side of the multimode optical fiber. It can thus be ascertained what modifications of the coherent light are necessary to obtain illumination of a single object point.

As an alternative or in addition to measuring the light transmission properties, the light transmission properties of the multimode optical fiber can also be calculated by modelling on the basis of the wave propagation.

In some embodiments, the multimode optical fiber is introduced into the sample to examine the sample. In this case, in particular a sharp edge between the light transmission surface and the light reflection surface at the distal end of the multimode optical fiber cuts through the sample. The sample material is thus not merely pushed to the side, but cut, as result of which the destruction of the sample is reduced.

In some embodiments, recordings of the sample are taken while the multimode optical fiber is being introduced into the sample, with the result that a recording of the sample along the path of the multimode optical fiber is produced. When the images obtained are being prepared, it is helpful when there is also information belonging to the respective image which specifies how far the multimode optical fiber was inserted into the sample, so that a combined image can be generated.

In some embodiments, the multimode optical fiber is rotated about its axis of rotation in relation to the sample. As a result, recordings of the sample in a cylindrical region around the distal end of the multimode optical fiber are obtained.

It is also possible to take recordings while the multimode optical fiber is being introduced into the probe and simultaneously rotated. As a result, a recording of a long cylindrical region of the sample is obtained.

It goes without saying that a preferred embodiment can also be obtained from a combination of dependent claims with the respective independent claim.

The invention will be described on the basis of exemplary embodiments depicted in the figures for the purpose of further clarification. These embodiments are to be understood only as examples and not as limitations.

DETAILED DESCRIPTION OF EMBODIMENTS

In the figures, the same reference signs characterize either the same elements or elements with an equivalent function. Elements already described are not necessarily described again in subsequent figures.

Figure 1:
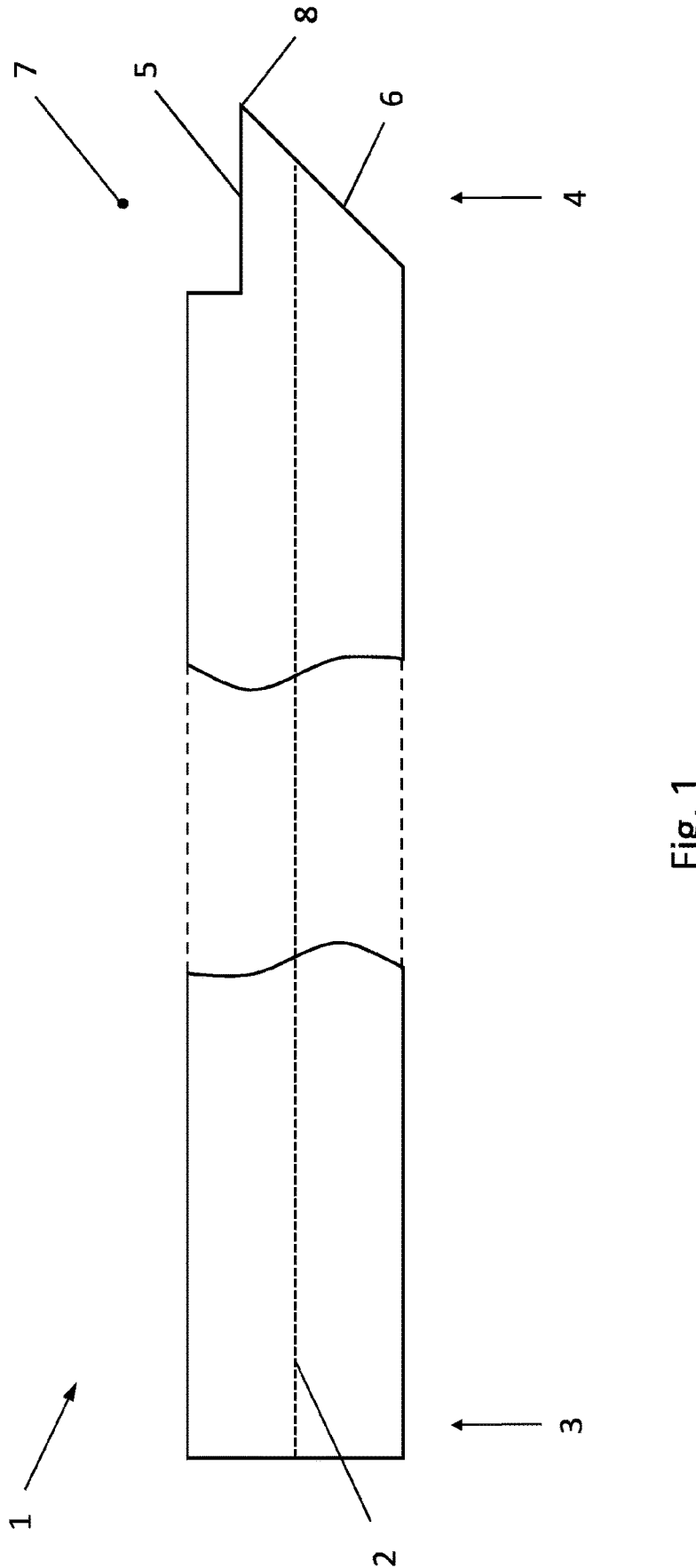
FIG. 1 shows a longitudinal section through one embodiment of a multimode optical fiber.

FIG. 1 shows a longitudinal section through one embodiment of a multimode optical fiber 1. The multimode optical fiber 1 has an optical axis 2, which corresponds to the axis of rotational symmetry in the case of a straight, non-curved multimode optical fiber 1.

In addition, the multimode optical fiber 1 has a proximal end 3. An endoscopic system is connected to the proximal end 3 for endoscopic examinations using the multimode optical fiber 1.

The multimode optical fiber 1 also has a distal end 4, which is opposite the proximal end 3. The distal end 4 is designed for introduction of the multimode optical fiber 1 into a sample. In this respect, the sample may be an inorganic or an organic sample, for example an animal or a human. The high resolution that can be obtained with an endoscopic system comprising a multimode optical fiber 1 makes it possible, for example, to examine neurons and the neuronal network, for example in the brain of the sample.

The distal end 4 has a light transmission surface 5 which extends substantially parallel to the optical axis 2. Light can exit the multimode optical fiber 1 in a well-defined way or enter the multimode optical fiber 1 through the light transmission surface 5.

The light transmission surface 5 may also be provided with a coating, in particular with a dielectric coating. This improves the light transmission and reduces disruptive reflections.

In addition, the distal end 4 has a light reflection surface 6. In this respect, the light reflection surface 6 lies such that the optical axis 2, a normal to the light transmission surface 5 and a normal to the light reflection surface 6 lie in one plane. The angle between the light reflection surface 6 and the optical axis 2 is approximately 45° here. Light entering the multimode optical fiber 1 through the light transmission surface 5 is reflected by the light reflection surface 6 in such a way that it can be conveyed by the multimode optical fiber 1. Similarly, light coming from the proximal end 3 of the multimode optical fiber 1 is reflected by the light reflection surface 6 in such a way that it can exit the multimode optical fiber 1 through the light transmission surface 5.

The light reflection surface 6 may also be provided with a coating, in particular with a metallic and/or dielectric coating, with the result that the light reflection at the light reflection surface 6 and thus the light yield are improved.

Owing to the arrangement of the light reflection surface 6 and the light transmission surface 5, the multimode optical fiber 1 can be used to examine object points 7 which are radially remote from the optical axis 2 in the region of the distal end 4 in front of the light transmission surface 5. Since it is mainly sample material which is in front of the multimode optical fiber 1 that is destroyed when the multimode optical fiber 1 is being introduced in a sample, this lateral examination makes it possible to examine sample material which has not been destroyed or is only slightly destroyed.

In addition, a sharp edge 8 is formed between the light transmission surface 5 and the light reflection surface 6. This sharp edge 8 can cut through the sample material when the multimode optical fiber 1 is being introduced into the sample. By contrast to pushing a blunt end through the sample, the sample is destroyed less as a result.

Figure 2:
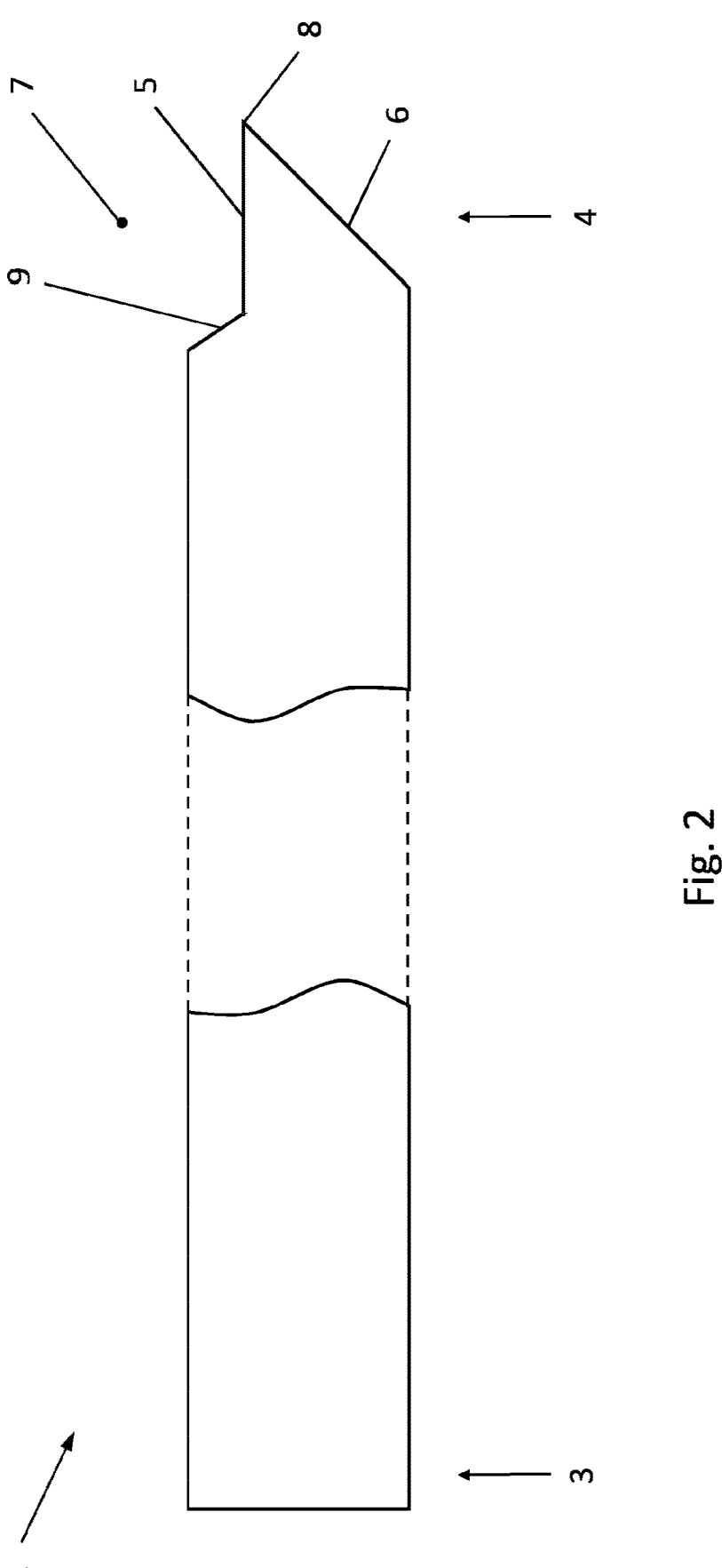
FIG. 2 shows a longitudinal section through another embodiment of a multimode optical fiber.

In the exemplary embodiment illustrated in FIG. 2 of a multimode optical fiber 1, by contrast to the exemplary embodiment of FIG. 1 the multimode optical fiber 1 has a beveled surface 9, which adjoins the light transmission surface 5 in the direction of the proximal end 3. This beveled surface 9 makes it easier to introduce the multimode optical fiber 1 into the sample and reduces the destruction of the sample.

Figure 3:
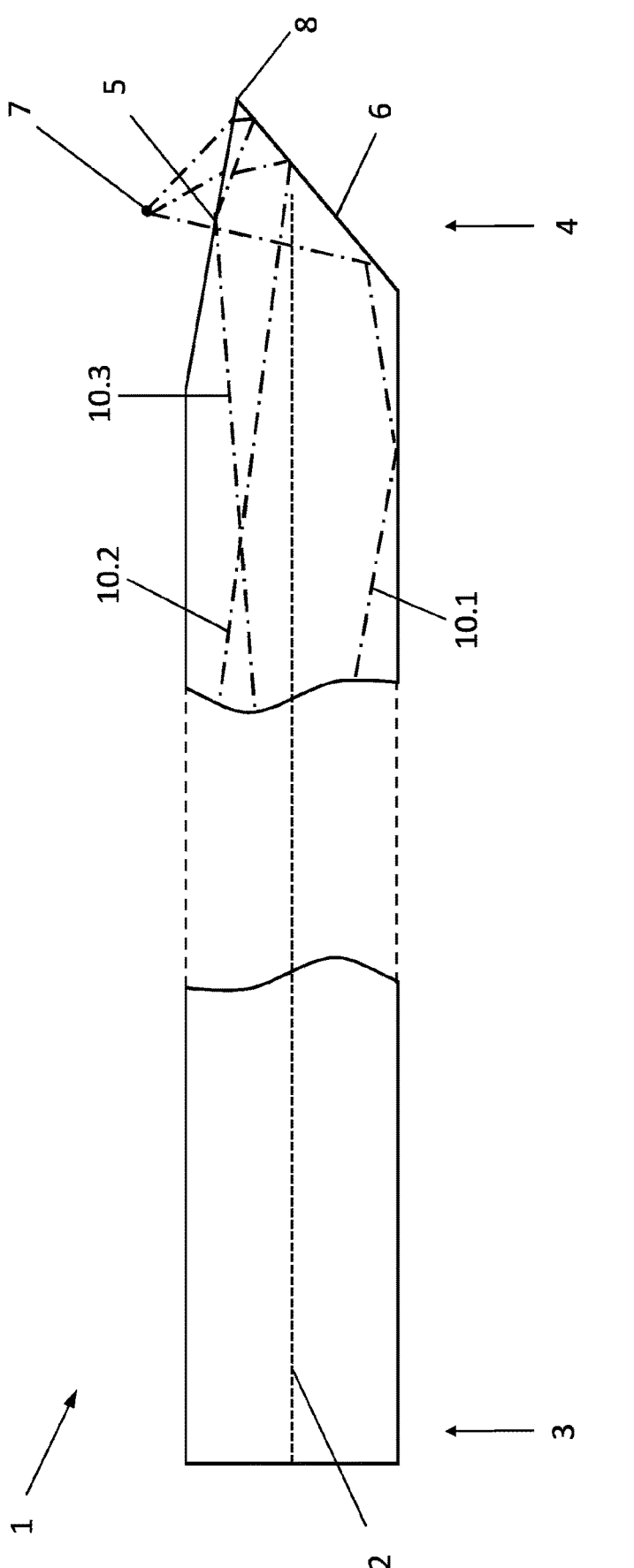
FIG. 3 shows a longitudinal section through yet another embodiment of a multimode optical fiber.

FIG. 3 shows a longitudinal section through another exemplary embodiment of a multimode optical fiber 1. Here, the light transmission surface 5 is inclined by a small angle in relation to the optical axis 2. A beveled surface 9 as in the exemplary embodiment of FIG. 2 is thus no longer necessary. In addition, the inclination of the light reflection surface 6 is adapted in such a way that light entering the multimode optical fiber 1 through the light transmission surface 5 is introduced optimally into the multimode optical fiber 1, and the same applies for light exiting through the light transmission surface 5.

The inclination of the light transmission surface 5 moreover results in the advantage that light emanating from an object point 7 can enter the multimode optical fiber 1 through the light transmission surface 5, can be reflected by the light reflection surface 6 and can be totally reflected at the light transmission surface 5 again, before it is input coupled into the multimode optical fiber 1 as light mode. The light path may of course also run in the opposite direction. As a result, light from a relatively large angle range can be input coupled into the multimode optical fiber 1, this leading to an increase in the resolution. Three exemplary light beams 10, including a light beam 10.3, which is part of the expanded mode, are depicted in FIG. 3.

Figure 4:
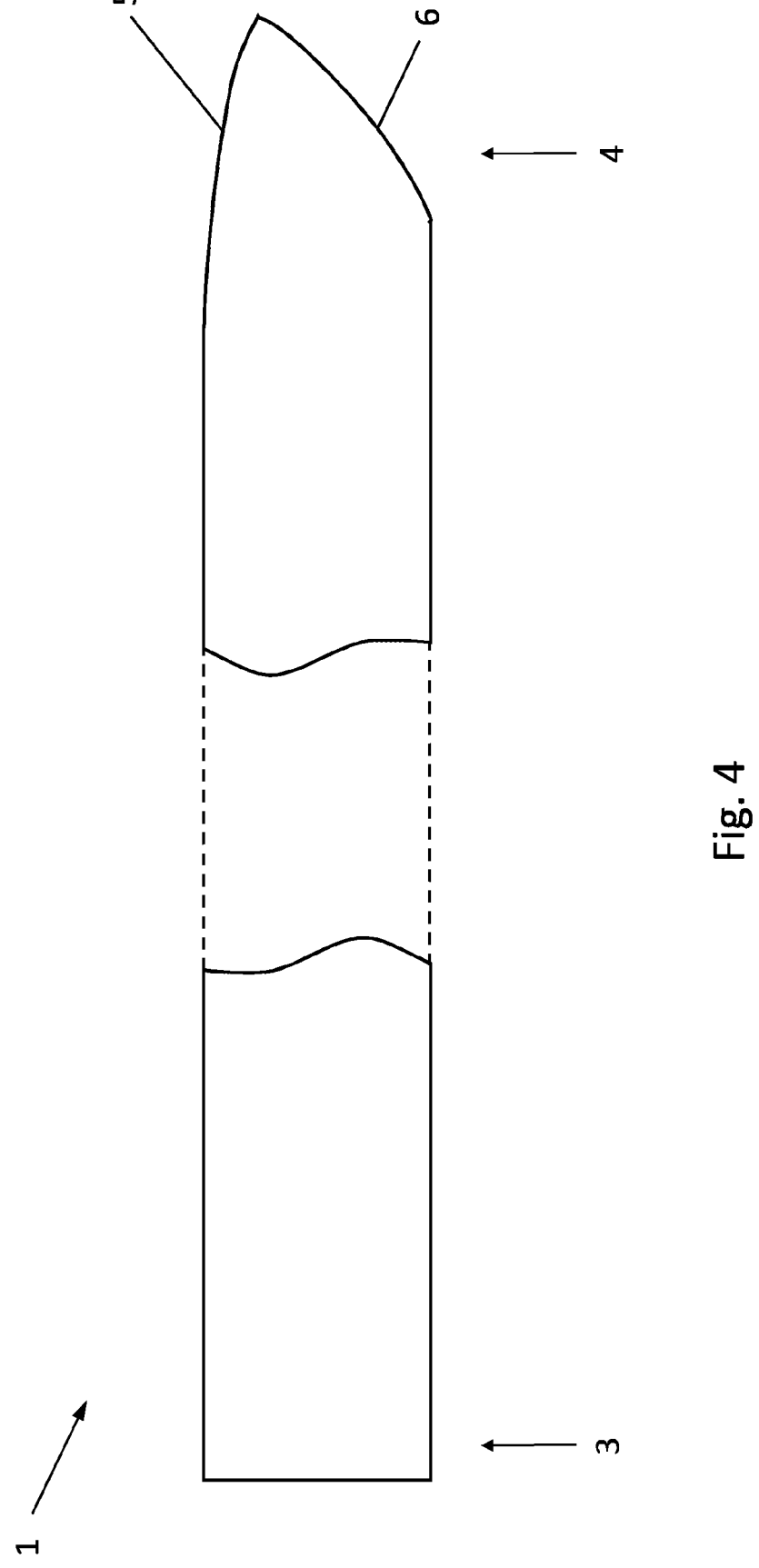
FIG. 4 shows a longitudinal section through yet another embodiment of a multimode optical fiber.

FIG. 4 shows yet another exemplary embodiment of a multimode optical fiber 1. By comparison to the exemplary embodiment of FIG. 3, both the light transmission surface 5 and the light reflection surface 6 are not flat surfaces, but spherical segment surfaces. It is also conceivable that one of the two surfaces is a flat surface and the other one is a spherical segment surface. In addition, it is possible that one or both of the surfaces is a paraboloid segment surface. This shaping of the light transmission surface 5 and/or light reflection surface 6 modifies the beam path of the entering and exiting light, for example to enable a particular examination.

Figure 5:
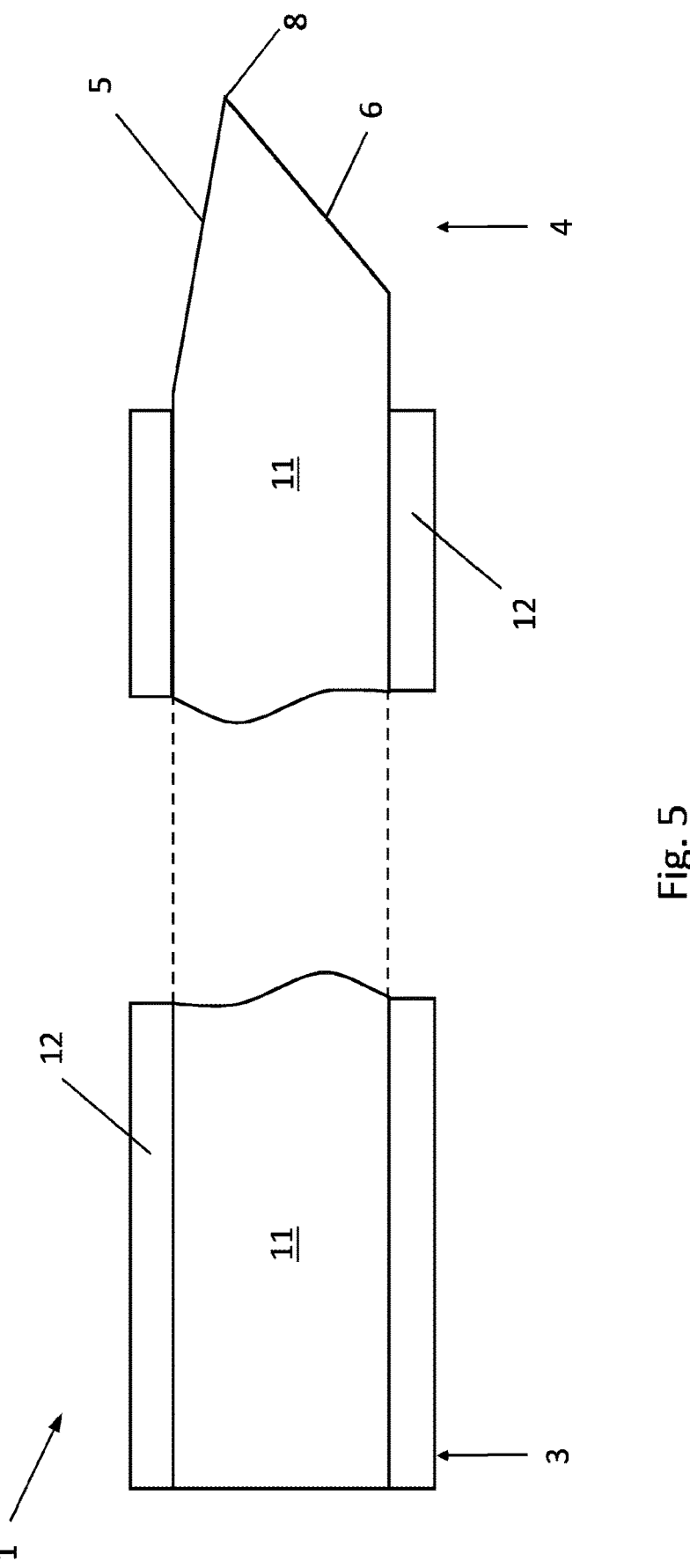
FIG. 5 shows a longitudinal section through yet another embodiment of a multimode optical fiber.

FIG. 5 shows yet another exemplary embodiment of a multimode optical fiber 1, it explicitly being shown that a fiber core 11 is surrounded by a cladding 12. In this respect, the cladding 12 ensures that the total reflection of the light in the fiber core 11 is independent of the medium surrounding the multimode optical fiber 1 and thus, for example, disruptions caused by a changing medium along the multimode optical fiber 1 are prevented. The light transmission surface 5 is also a boundary surface of the fiber core 11, that is to say the fiber core 11 is delimited, inter alia, by the light transmission surface 5.

Figure 6:
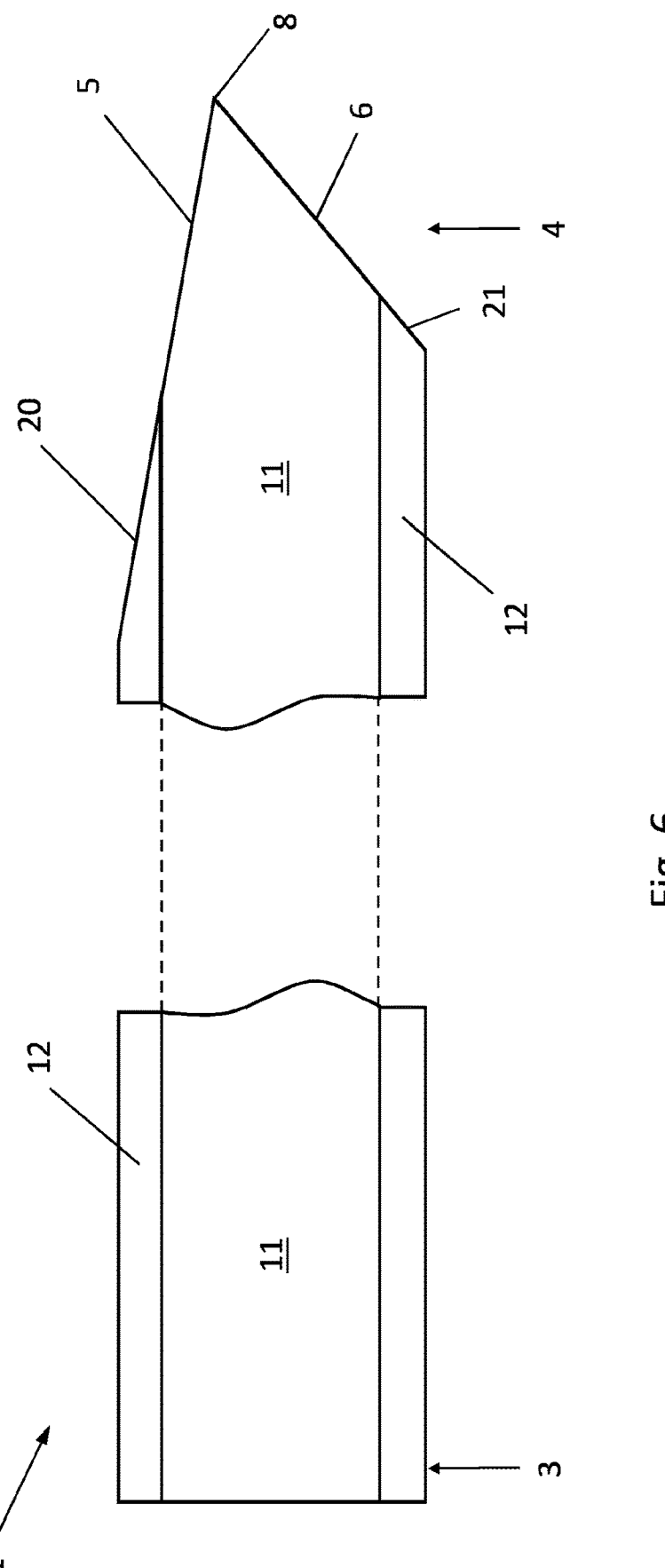
FIG. 6 shows a longitudinal section through yet another embodiment of a multimode optical fiber and FIG. 7 shows a schematic view of one embodiment of an endoscopic system.

FIG. 6 shows yet another exemplary embodiment of a multimode optical fiber 1, in the case of which the light transmission surface 5 continues in the cladding 12 as expanded light transmission surface 20. In addition, the light reflection surface 6 continues in the cladding 12 as expanded light reflection surface 21.

Figure 7:
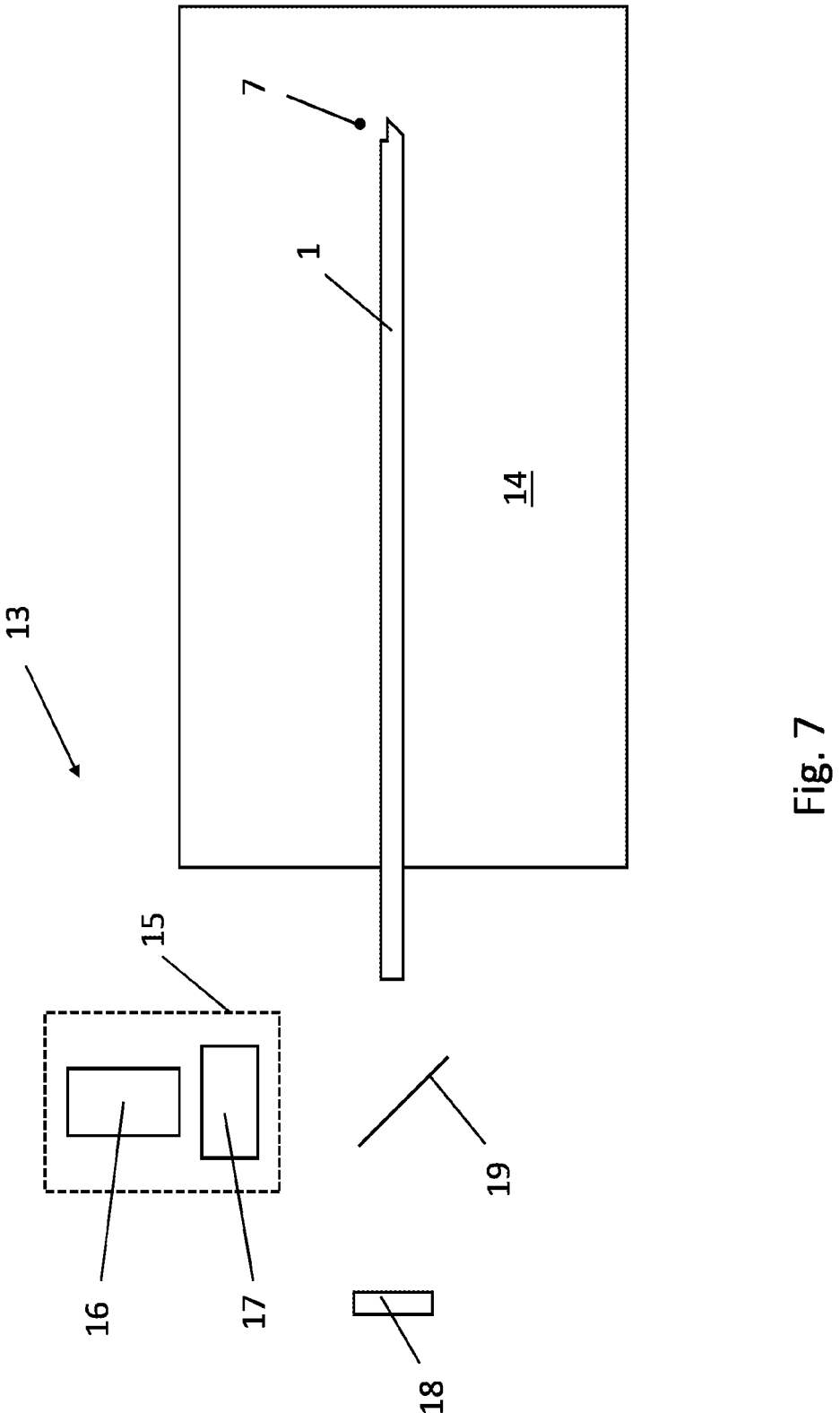

Lastly, FIG. 7 shows an endoscopic system 13 for examining a sample 14. A multimode optical fiber 1 is introduced into the sample 14 and aligned to examine object points 7 which are radially remote from the optical axis 2 of the multimode optical fiber 1 and are arranged in front of the light transmission surface 5.

The endoscopic system 13 also comprises a coherent light source 15, which is illustrated schematically here as a laser 16 and a modifier 17, with the modifier 17 being designed to modify the light wavefront emitted by the laser 16.

In addition, the endoscopic system 13 comprises a photodetector 18. Moreover, a beam splitter 19 is arranged such that it is possible both to radiate light from the coherent light source 15 into the multimode optical fiber 1 and to use the photodetector 18 to detect light coming from the multimode optical fiber 1.

During operation of the endoscopic system 13, the coherent light source 15 is operated in such a way that a multiplicity of object points 7 in the sample are illuminated one after another and the answering light emitted by each object point 7 is detected by means of the photodetector 18.

The multimode optical fiber 1 may moreover be rotated about its optical axis 2 in relation to the sample 14, with the result that it is possible for an examination to be carried out not just of object points 7 in a plane in front of the light transmission surface 5 but cylindrically about the distal end 4 of the multimode optical fiber 1.

In addition, it is possible to take recordings already when the multimode optical fiber 1 is being introduced into the sample 14, with the result that a long recording along the multimode optical fiber 1 is produced.

The invention claimed is:

1. An endoscopic system for examining a sample, comprising:
    a coherent light source;
    a photodetector; and
    a multimode optical fiber with an optical axis and having a single fiber core surrounded by a cladding, the multimode optical fiber comprising:
    a proximal end configured to be connected to the endoscopic system; and
    a distal end configured to be inserted into the sample, wherein the distal end has a light transmission surface which extends essentially parallel to the optical axis, and is designed to transmit light radially to the optical axis,
    wherein the light transmission surface is (i) at least one of an approximately flat surface, a spherical segment surface or a paraboloid segment surface, and (ii) an interface of the fiber core,
    wherein the distal end has a light reflection surface which approximately runs such that (i) the optical axis at the distal end, a normal to the light transmission surface and a normal to the light reflection surface lie approximately in one plane, and (ii) an angle between the light-reflecting surface and the optical axis is between 30° and 60°, and
    wherein the coherent light source is arranged to introduce the light into the proximal end of the multimode optical fiber, and the photodetector is arranged to detect a multimode light emerging from the proximal end emitted by the multimode optical fiber.

2. A method for examining a sample using an endoscopic system which comprises a coherent light source, a photodetector, and a multimode optical fiber with an optical axis and having a single fiber core surrounded by a cladding, the multimode optical fiber comprising:
    a proximal end configured to be connected to the endoscopic system; and
    a distal end configured to be inserted into the sample,
    wherein the distal end has a light transmission surface which extends essentially parallel to the optical axis, and is designed to transmit light radially to the optical axis, wherein the light transmission surface is (i) at least one of an approximately flat surface, a spherical segment surface or a paraboloid segment surface, and (ii) an interface of the fiber core,
    wherein the distal end has a light reflection surface which approximately runs such that (i) the optical axis at the distal end, a normal to the light transmission surface and a normal to the light reflection surface lie approximately in one plane, and (ii) an angle between the light-reflecting surface and the optical axis is between 30° and 60°,
    wherein the coherent light source is arranged to introduce the light into the proximal end of the multimode optical fiber, and the photodetector is arranged to detect a multimode light emerging from the proximal end emitted by the optical fiber, and
    wherein the method comprises illuminating a large number of object points in the sample using the coherent light source through the multimode optical fiber, such that light is reflected from the object points through the multimode optical fiber and detected using the photodetector.

3. The method according to claim 2, wherein light transmission properties of the multimode optical fiber are at least one of measured or calculated prior to inspecting the sample.

4. The method according to claim 2, further comprising inserting the multimode optical fiber into the sample such that a sharp edge between the light transmission surface and the light reflection surface at the distal end of the multimode optical fiber cuts through the sample.

5. The method according to claim 4, further comprising recordings information regarding the sample during the insertion of the multimode optical fiber into the sample, such that the information regarding the sample is recorded along a path of the multimode optical fiber.

6. The method according to claim 2, further comprising:

rotating the multimode optical fiber about its optical axis with respect to the sample; and obtaining images of the sample in a cylindrical region around the distal end of the multimode optical fiber during the rotation.

\* \* \* \* \*